United States Patent
Peltola et al.

(10) Patent No.: US 12,138,478 B2
(45) Date of Patent: Nov. 12, 2024

(54) METHOD AND APPARATUS TO OPTIMIZE A RADIATION TREATMENT PLAN

(71) Applicant: Siemens Healthineers International AG, Steinhausen (CH)

(72) Inventors: Jarkko Peltola, Tuusula (FI); Marko Rusanen, Espoo (FI); Heini Hyvönen, Helsinki (FI); Tuomas Tallinen, Espoo (FI); Christopher Boylan, Helsinki (FI)

(73) Assignee: Siemens Healthineers International AG, Steinhausen (CH)

(*) Notice: Subject to any disclaimer, the term of this patent is extended or adjusted under 35 U.S.C. 154(b) by 387 days.

(21) Appl. No.: 17/555,782

(22) Filed: Dec. 20, 2021

(65) Prior Publication Data
US 2023/0191151 A1    Jun. 22, 2023

(51) Int. Cl.
*A61N 5/00*    (2006.01)
*A61N 5/10*    (2006.01)

(52) U.S. Cl.
CPC ......... *A61N 5/1031* (2013.01); *A61N 5/1028* (2013.01); *A61N 5/1045* (2013.01); *A61N 5/1048* (2013.01); *A61N 2005/1074* (2013.01)

(58) Field of Classification Search
None
See application file for complete search history.

(56) References Cited

U.S. PATENT DOCUMENTS

2015/0335914 A1    11/2015    Otto
2019/0255362 A1*    8/2019    Voronenko ........... A61N 5/1071

OTHER PUBLICATIONS

Zygmanski, Piotr et al.: "A volumetric-modulated arc therapy using sub-conformal dynamic arc with a monotonic dynamic multileaf collimator modulation; volumetric-modulated arc therapy using sub-conformal dynamic arc with a monotonic dMLC modulation", Physics :In Medicine and Biology, :Institute of Physics Publishing, Bristol GB, vol. 53, No. 22, Nov. 21, 2008 (Nov. 21, 2008), pp. 6395-6417, XP020141510, :ISSN: 0031-9155, doi: 10.1088/0031-9155/53/22/009.
International Search Report and Written Opinion from PCT/EP2022/086630 mailed Apr. 17, 2023; 13 pages.

* cited by examiner

*Primary Examiner* — Hoon K Song
(74) *Attorney, Agent, or Firm* — Fitch, Even, Tabin & Flannery LLP

(57) ABSTRACT

Patient information for a particular patient, radiation treatment information, and information regarding a particular radiation treatment platform that includes at least one multi-leaf collimator are each accessed. These teachings then provide for optimizing a radiation treatment plan to dose at least one treatment volume in the particular patient using the particular radiation treatment platform as a function of the patient information, the radiation treatment information, and the information regarding the particular radiation treatment platform, wherein the optimizing does not include optimizing movement of any leaves of the multi-leaf collimator.

14 Claims, 2 Drawing Sheets

METHOD AND APPARATUS TO OPTIMIZE A RADIATION TREATMENT PLAN

TECHNICAL FIELD

These teachings relate generally to treating a patient's planning target volume with energy pursuant to an energy-based treatment plan, and more particularly to optimizing such a plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called energy-based treatment plan often serves in the foregoing regards.

An energy-based treatment plan such as a radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters such as individual collimating leaf positions (often while observing one or more corresponding limits in these regards) and mathematically calculating a likely corresponding treatment result to identify a given set of treatment parameters that represent a good compromise between the desired therapeutic result and avoidance of undesired collateral effects.

Unfortunately, existing planning techniques do not necessarily address all potential needs for all potential patients in all potential application settings. As one example in these regards, in stereotactic body radiation therapy, the treatment aims to treat small tumor volumes with high doses per fraction. Treatment time in such therapy is important because patient position accuracy typically decreases as a function of time. Accordingly, short planning time is important in such cases. To avoid processing time associated with complex optimization algorithms, planning for such therapies typically uses conformal leaf sequences in combination with simple manual dose normalization. (As used herein, "conformal" refers to leaf apertures that conform to target projections in each field direction but which do not modulate the dose within the target.)

Unfortunately, when applied to arc fields, such an approach presumes a constant rate of Monitor Units (MU) per gantry rotation from all angles/fields. This can create non-optimal dose distribution for both target volumes and normal tissue.

BRIEF DESCRIPTION OF THE DRAWINGS

The above needs are at least partially met through provision of the method and apparatus to optimize a radiation treatment plan described in the following detailed description, particularly when studied in conjunction with the drawings, wherein.

Figure 1:
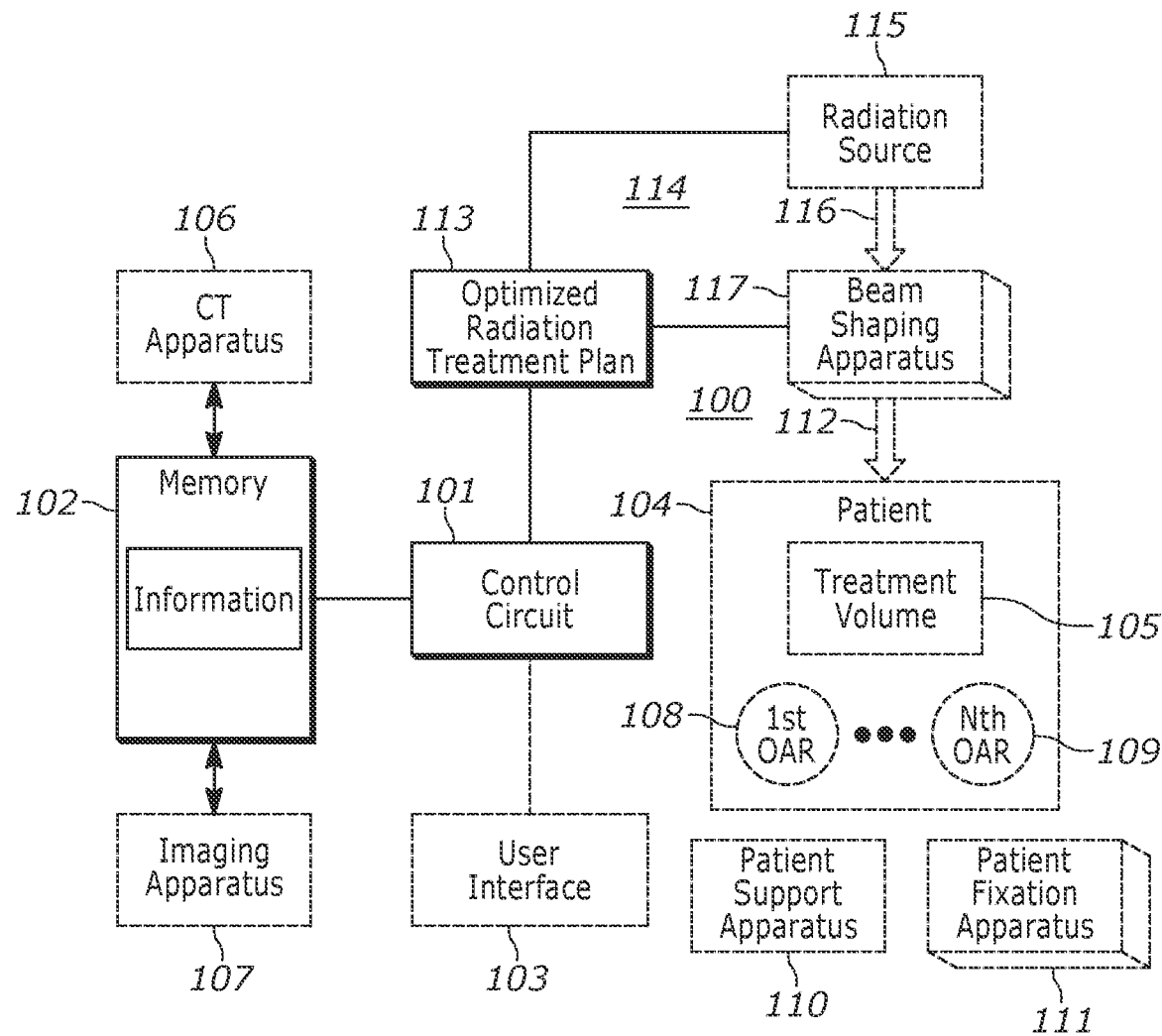
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate optimizing a patient treatment plan to administer therapeutic energy to a particular patient.

By one approach, these teachings provide for accessing each of patient information for a particular patient, radiation treatment information, and information regarding a particular radiation treatment platform that includes at least one multi-leaf collimator. These teachings then provide for optimizing a radiation treatment plan to dose at least one treatment volume in the particular patient using the particular radiation treatment platform as a function of the patient information, the radiation treatment information, and the information regarding the particular radiation treatment platform, wherein the optimizing does not include optimizing movement of any leaves of the multi-leaf collimator.

By one approach, the aforementioned optimizing includes outputting a radiation treatment plan that comprises a plurality of conformal arc fields. By one approach, the foregoing information regarding a particular radiation treatment platform comprises, at least in part, a set of user-specified treatment arc fields. At least two of those fields can optionally comprise treatment arc fields that have differing iso centers.

If desired, the output radiation treatment plan may further comprise variable rate of monitor units per control point. In a case of an arc field the rate is typically described as MU per gantry rotation (MU/deg). Accordingly, the aforementioned optimizing can comprise optimizing the radiation treatment plan as a function, at least in part, of monitor unit modulation (modulating the MU/deg per control point, or put otherwise, the meterset weight per control point). The foregoing may include optimizing monitor unit modulation as a function of at least one target coverage metric and one normal tissue treatment objective.

By one approach, the aforementioned optimizing further does not include optimizing movement of at least one jaw that shapes and/or modulates the radiation beam. By one approach, the foregoing optimizing does not include any cost function as a function of dose that corresponds to movement of any leaves of the multi-leaf collimator, movement of jaw positions, or collimator angles.

So configured, these teachings have the benefits associated with conformal leaf sequence-based therapies (including only requiring short processing times to develop and administer the respective radiation treatment plan) while also utilizing some optimization approaches that provide for a more careful administration of dosing to both the treatment volume and normal tissues including organs-at-risk.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as patient information for a particular patient, radiation treatment information, and information regarding a particular radiation treatment platform that includes at least one multi-leaf collimator, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan 113 (such as, for example, an optimized radiation treatment plan). This energy-based treatment plan 113 typically comprises specified values for each of a variety of treatment-platform parameters during each of a plurality of sequential exposure fields. In this case the energy-based treatment plan 113 is generated through an optimization process. Various automated optimization processes specifically configured to generate such an energy-based treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. These teachings are generally applicable for use with any of a wide variety of radiation treatment platforms. In a typical application setting the radiation treatment platform 114 will include a radiation source 115. The radiation source 115 can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

By one approach this energy source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the energy source 115 along that arcuate pathway, and may accordingly control when the energy source 115 starts moving, stops moving, accelerates, de-accelerates, and/or a velocity at which the energy source 115 travels along the arcuate pathway.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the energy source 115, and one or more energy-shaping apparatuses 117 (for example, beam-shaping apparatuses such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
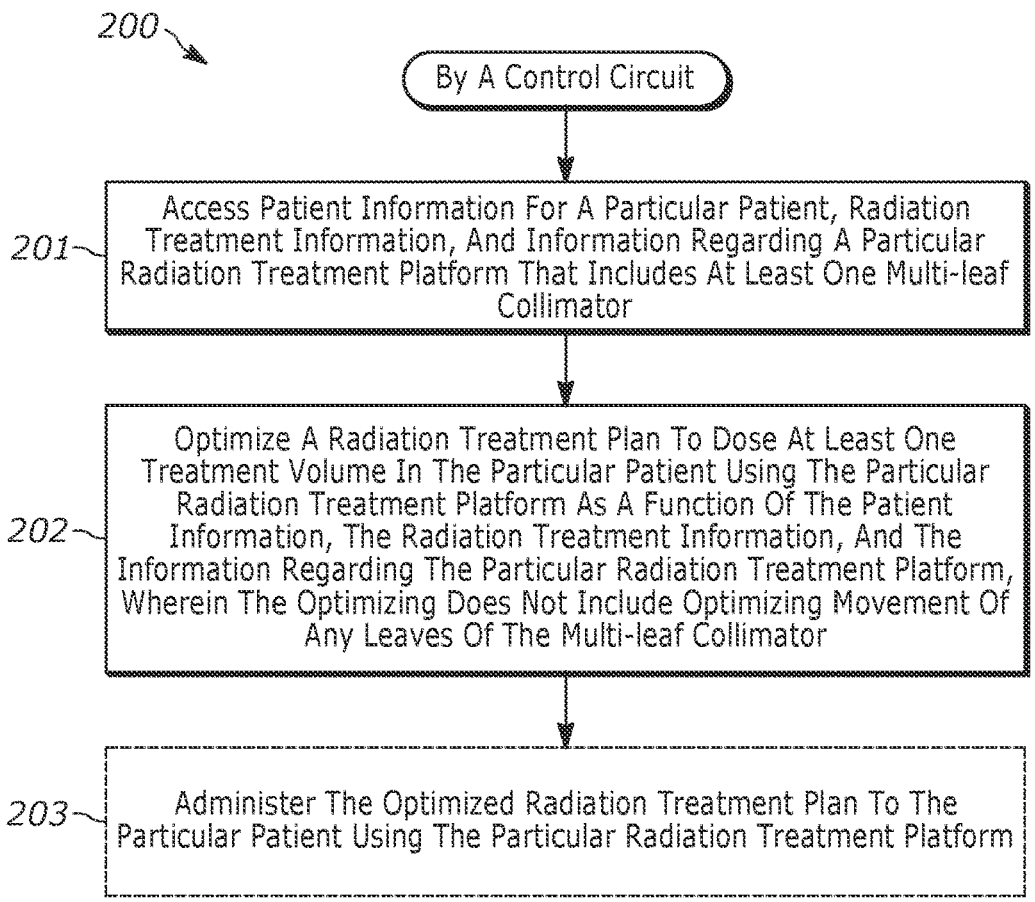
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described.

At block 201, this process 200 provides for accessing patient information for a particular patient 104, radiation treatment information, and information regarding a particular radiation treatment platform 114 that includes at least one multi-leaf collimator. This activity may comprise the control circuit 101 accessing the above-described memory 102 to obtain the described information. By one approach, the aforementioned information regarding a particular radiation treatment platform 114 can comprise, at least in part, a set of user-specified treatment arc fields. The latter may comprise, for example, at least two treatment arc fields that have differing isocenters.

At block 202, the control circuit 101 then optimizes a radiation treatment plan to dose at least one treatment volume 105 in the particular patient 104 using the particular radiation treatment platform 114 as a function of the aforementioned patient information, radiation treatment information, and information regarding the particular radiation treatment platform.

This optimizing, however, does not include optimizing movement of any leaves of the multi-leaf collimator. The latter exclusion constitutes a significant break with prior art practice when optimizing a radiation treatment plan that employs use of a multi-leaf collimator.

In some application settings, the radiation treatment platform 114 may include beam shaping apparatuses 117 in addition to a multi-leaf collimator. In such a case, the radiation treatment plan to be optimized may also additionally presume use of at least one jaw and at least one collimator angle to facilitate conformally shaping a radiation beam with respect to a given field of view of the treatment volume 105. Notwithstanding the use of at least one multi-leaf collimator, at least one jaw, and at least one collimator angle to facilitate conformally shaping radiation beams with respect to given fields of view, these teachings will accommodate conducting the foregoing optimization without including optimization of any movement of any multi-leaf collimator leaves, jaws, or collimator angles. In some application settings, the given field of view of the treatment volume 105 can be partially masked from some angles by a field of view of a user specified organ-at-risk. An example of this would be a pace-maker structure that needs to be shielded from any radiation.

To put this another way, the foregoing optimization of the radiation treatment plan can be undertaken such that the optimizing does not include any cost function as a function of a dose that corresponds to movement of any leaves of a multi-leaf collimator, movement of jaw positions, or collimator angles. In such a case, these other non-optimized features of the radiation treatment platform 114 can simply be set by only applying geometric conformality to the target(s) in a two-dimensional multi-leaf collimator-plane.

By one approach, the foregoing optimization of the radiation treatment plan can comprise optimizing the radiation treatment plan as a function, at least in part, of monitor unit modulation. The foregoing can comprise optimizing monitor unit modulation as a function of at least one target coverage metric and one normal tissue treatment objective. By one approach the foregoing may comprise using monitor units (or meterset weight per control point) as the only parameter that is being optimized using a cost function (as a function of dose).

By one approach, the activity of block 202 can include outputting a radiation treatment plan 113 that comprises a plurality of conformal arc fields. By one approach, the latter can comprise a plurality of conformal arc fields with corresponding variable monitor units per control points.

Figure 3:
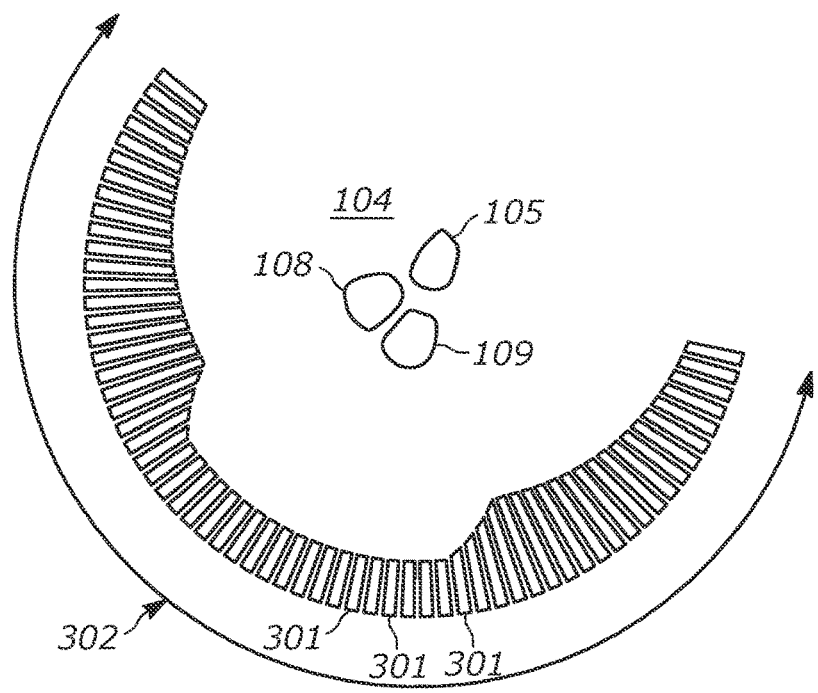
FIG. 3 comprises an illustrative screenshot as configured in accordance with various embodiments of these teachings.

The foregoing activities can yield and produce an optimized radiation treatment plan in a period of time that is short enough to fall within the expectation range of ordinary stereotactic body radiation therapy planning while also providing considerably greater flexibility to control dosing with control point granularity. FIG. 3 presents an exemplary illustrative example in these regards. As the radiation source 115 travels in an arc 302 around the patient 104, the dosing (as represented on a control point by control point basis by reference 301) can be varied depending upon the control point/field-of-view to thereby, for example, reduce dosing when normal tissue (including organs-at-risk 108, 109) are exposed and/or increase dosing when untargeted tissue is less at risk.

At optional block 203, this process 200 can then provide for administering the resultant optimized radiation treatment plan to the aforementioned patient using the aforementioned radiation treatment platform.

Those skilled in the art will appreciate that while these teachings do not change the essential nature of conformal arc treatment techniques, the planning quality can be dramatically improved.

Generally speaking, and by one approach, these teachings can be implemented by first asking the user to define an arc field setup (by establishing, for example, start and end angles regarding a gantry, collimator, patient support surface, and so forth) and a requirement for the target dose conformality as they would manually set when planning normal manual conformal arc cases. (It will be understood that these teachings will also accommodate the automatic determination of part or all of the arc field setup.) Examples in these regards might include having the prescribed dose volume conform to the target structure, or having a certain isodose line (such as 80%) cover all parts of the target.

After this, the plan optimization control circuit can generate and set conformal arcs per field as the starting point and then automatically optimize the meterset weights per control point in the arc fields, so that the target dose conformality requirement is fulfilled while the dose outside the target is minimized. No leaf position is optimized during the optimization, which separates this from the other arc optimization techniques. The end result is the same familiar arc setup that these users expect to see but the dose is better due to the added dimensions and the dose can also be correctly normalized.

Those skilled in the art will recognize that a wide variety of modifications, alterations, and combinations can be made with respect to the above-described embodiments without departing from the scope of the invention. For example, by one approach, the aforementioned optimization may be carried out for some, but not all, multi-leaf collimator leaves. This might comprise, for example, optimizing only one leaf, only two leaves, no more than five leaves, no more than ten leaves, no more than fifteen leaves, no more than ten percent of the leaves, no more than twenty percent of the leaves, no more than thirty percent of the leaves no more than forty percent of the leaves, no more than fifty percent of the leaves, and so forth. Accordingly, such modifications, alterations, and combinations are to be viewed as being within the ambit of the inventive concept.

What is claimed is:

1. A method comprising:
   by a control circuit:
   accessing patient information for a particular patient, radiation treatment information, and information regarding a particular radiation treatment platform that includes at least one multi-leaf collimator;
   optimizing a radiation treatment plan to dose at least one treatment volume in the particular patient using the particular radiation treatment platform as a function of the patient information, the radiation treatment information, and the information regarding the particular radiation treatment platform, wherein the optimizing:
   does not include optimizing movement of any leaves of the multi-leaf collimator; and
   comprises optimizing the radiation treatment plan as a function, at least in part, of monitor unit modulation by optimizing monitor unit modulation as a function of a least one of at least one target coverage metric and at least one normal tissue treatment objective, with monitor units serving as an only parameter that is being optimized using a corresponding cost function.

2. The method of claim 1 wherein optimizing the radiation treatment plan includes outputting a radiation treatment plan that comprises a plurality of conformal arc fields.

3. The method of claim 2 wherein outputting the radiation treatment plan comprises outputting a radiation treatment plan that comprises a plurality of conformal arc fields with variable monitor unit per gantry rotation per control point.

4. The method of claim 1 wherein optimizing the radiation treatment plan comprises optimizing a radiation treatment plan that uses the multi-leaf collimator as well as at least one of at least one jaw and at least one collimator angle to conformally shape a radiation beam with respect to a given field of view of the treatment volume without also using the multi-leaf collimator or the at least one jaw to modulate the radiation beam.

5. The method of claim 1 wherein the information regarding a particular radiation treatment platform comprises, at least in part, a set of user-specified treatment arc fields.

6. The method of claim 5 wherein the set of user-specified treatment arc fields can include at least two treatment arc fields that have differing isocenters.

7. The method of claim 1 wherein the optimizing does not include any cost function as a function of dose that corresponds to movement of any leaves of the multi-leaf collimator, movement of jaw positions, or collimator angle.

8. An apparatus comprising:
   a memory having stored therein patient information for a particular patient, radiation treatment information, and information regarding a particular radiation treatment platform that includes at least one multi-leaf collimator;
   a control circuit operably coupled to the memory and configured to optimize a radiation treatment plan to dose at least one treatment volume in the particular patient using the particular radiation treatment platform as a function of the patient information, the radiation treatment information, and the information regarding the particular radiation treatment platform, wherein the optimizing:
   does not include optimizing movement of any leaves of the multi-leaf collimator; and
   comprises optimizing the radiation treatment plan as a function, at least in part, of monitor unit modulation by optimizing monitor unit modulation as a function of a least one of at least one target coverage metric and at least one normal tissue treatment objective, with monitor units serving as an only parameter that is being optimized using a corresponding cost function.

9. The apparatus of claim 8 wherein the control circuit is configured to optimize the radiation treatment plan by outputting a radiation treatment plan that comprises a plurality of conformal arc fields.

10. The apparatus of claim 9 wherein the control circuit is configured to output the radiation treatment plan by outputting a radiation treatment plan that comprises a plurality of conformal arc fields with variable monitor unit per gantry rotation per control point.

11. The apparatus of claim 8 wherein the control circuit is configured to optimize the radiation treatment plan by optimizing a radiation treatment plan that uses the multi-leaf collimator as well as at least one jaw and collimator angle to conformally shape a radiation beam with respect to a given field of view of the treatment volume without also using the multi-leaf collimator or the at least one jaw to modulate the radiation beam.

12. The apparatus of claim 8 wherein the information regarding a particular radiation treatment platform comprises, at least in part, a set of user-specified treatment arc fields.

13. The apparatus of claim 12 wherein the set of user-specified treatment arc fields can include at least two treatment arc fields that have differing isocenters.

14. The apparatus of claim 8 wherein the control circuit is configured such that the optimizing does not include any cost function as a function of dose that corresponds to movement of any leaves of the multi-leaf collimator, movement of jaw positions, or collimator angle.

* * * * *